United States Patent [19]
Kremer et al.

[11] Patent Number: 5,586,980
[45] Date of Patent: Dec. 24, 1996

[54] MICROKERATOME

[76] Inventors: Frederic B. Kremer, 887 Roscommon Rd., Bryn Mawr, Pa. 19010; Harold E. Clupper, Little Shiloh Rd., West Chester, Pa. 19380

[21] Appl. No.: 323,177

[22] Filed: Oct. 14, 1994

[51] Int. Cl.$^6$ .............................. A61F 9/00; A61N 5/06
[52] U.S. Cl. ............................................................. 606/4
[58] Field of Search .................... 606/4, 5, 6, 107, 606/166, 167; 604/22, 174, 170

[56] References Cited

U.S. PATENT DOCUMENTS

| | | | |
|---|---|---|---|
| 4,526,171 | 7/1985 | Schachar | 606/166 |
| 4,546,773 | 10/1985 | Kremer et al. | |
| 4,598,714 | 7/1986 | Kremer et al. | |
| 4,688,570 | 8/1987 | Kramer et al. | 606/166 |
| 4,903,695 | 2/1990 | Warner et al. | 606/4 |
| 5,222,960 | 6/1993 | Poley | 606/107 |

FOREIGN PATENT DOCUMENTS

| | | | |
|---|---|---|---|
| 0442156 | 8/1991 | European Pat. Off. | 606/5 |
| 0531756 | 3/1993 | European Pat. Off. | 606/4 |
| 9305738 | 4/1993 | WIPO | 606/4 |

OTHER PUBLICATIONS

Pallikaris et al., *Excimer Laser In Situ Keratomileusis and Photorefractive keratectomy for Correction of High Myopia*, Journal of Refractive & Corneal Surgery, vol. 10, Sep.–Oct. 1994, pp. 498–510.

Barraquer et al., *Lamellar Keratoplasty (Special Techniques)*, Annals of Ophthalmology, Jun. 1972.

Kremer, *ALK–E: As Good as Advertise*, Review of Ophthalmology, Aug. 1994, p. 46.

Ruiz, "*Flap and Zap*": *Is the Next Radial K?*, Review of Ophthalmology, Aug. 1994, pp. 44–45.

Rozakis et al., *Refractive Lamellar Keratoplasty*, Slack Incorporated, 1994, (Chapters 1–2, 5–10 & 13) pp. 1–16, 19–32, 45–99 and 125–137.

Barraquer, *Keratomileusis for Myopia and Aphakia*, Ophthalmology, vol. 88, No. 8, Aug. 1981, pp. 701–708.

Burillon et al., *Combined Epikeratoplasty and Homoplastic Keratophakia for Correction of Aphakia: Double Curve Effect*, Refractive & Corneal Surgery, vol. 9, May–Jun. 1993, pp. 214–218.

Barraquer, *Results of Hypermetropic Keratomileusis*, 1980–1981, International Ophthalmology Clinics 23(3), 1983, pp. 25–44.

Unknown, *Excimer Laser Photorefractive Keratectomy*, Refractive Surgery, Chapt. 24, pp. 680–691.

Schanzlin, *Epikeratophakia and Keratomileusis*, Refractive Surgery, Chap. 24, pp. 696–699.

*Primary Examiner*—Angela D. Sykes
*Assistant Examiner*—Sonya Harris-Ogugua
*Attorney, Agent, or Firm*—Volpe & Koenig, P.C.

[57] ABSTRACT

A micro-keratome device for performing eye surgery is disclosed. The device is comprised of a vacuum ring, an applanation shoe and a cutting blade. The cutting blade and applanation shoe are mounted on the vacuum ring with the cutting blade being pivotally mounted to the applanation shoe so that movement of the cutting blade, while the vacuum ring is still mounted to a patient's eye, permits the user to have an unobstructed path to that portion of the eye exposed by the cutting blade. In a further embodiment, the device includes a guard, mounted at one end of the applanation shoe, which collects, protects and positions the previously cut portion of eye tissue.

44 Claims, 5 Drawing Sheets

5,586,980

MICROKERATOME

This invention is directed to a corneal surgery apparatus. In particular, this invention is related to a micro-keratome instrument.

BACKGROUND OF THE INVENTION

Refractive surgery is a known method of treating myopia, hyperopia, astigmatism, and certain corneal abnormalities in humans. This process involves reshaping various layers of the cornea to change the refractive surface thereof. Refractive surgical methods include radial keratotomy, radial keratectomy, lamellar keratectomy, lamellar keratotomy and others. One procedure for performing laser keratectomy (reprofiling of the cornea) by laser ablation comprises removal and discarding the central epithelium and then exposing the underlying surface to the laser.

Prior art micro-keratome instruments comprise a vacuum ring, a knife blade, and an applanation shoe assembled onto the vacuum ring. The knife blade makes a single cut at the appropriate corneal depth as determined by the height of the applanation shoe. In some procedures the cut-away layer is entirely detached from the remainder of the cornea. Generally, the cut is such that the membrane layers to be removed are not completely detached from the cornea, but remain connected by a flap allowing the membrane to be folded to one side, while underlying stromal issue is removed. After cutting, the knife blade is retracted allowing the membrane to temporarily settle back to its original position. Then the superficial corneal section is hinged to one side. A second corneal incision is made removing corneal stromal tissue from the underlying bed. The superficial corneal section is then folded back into its original position.

Prior art micro-keratome instruments require a transverse oscillatory cutting motion be used to insure accurate cutting of the cornea, and to prevent deforming or bunching of the corneal membranes during cutting. These complex cutting motions are a result of the steel blades used in conventional devices. Additionally, the steel blades have limited life spans and require regular replacement.

Conventional cutting devices stabilize the globe by vacuum-mounting the keratome to the globe. However, prior to making the second corneal incision to excise corneal tissue from the underlying corneal bed, the cutting device must be removed. The vacuum ring may remain on the eye after removing the cutting device in some surgical procedures. Hence, the vacuum-induced globe stabilization is terminated. With the globe in this state, the corneal flap created by cutting can be manually folded away. Hence, damage to the flap could occur during this time. Moreover, the delay encountered by removing the cutting apparatus can result in changes in hydration of the corneal flap during apparatus removal. This may also result in epithelial cells being deposited in the interface. The corneal flaps are difficult to reset into the original position. Such repositioning is even more difficult in those procedures wherein the lamellar incision removes an entire area of the cornea (no connecting area) which is removed in the form of a corneal cap.

OBJECTS OF THE INVENTION

It is an object of the invention to provide a micro-keratome instrument able to cut into the cornea without deforming or bunching up the membrane during the cut.

It is a further object of this invention to provide a micro-keratome instrument that does not have to be removed from the eye between producing the incision and further treatment of the cornea.

It is a still further object of the invention to provide a micro-keratome instrument able to retract the corneal flap without applying undue stress to the connecting portion of the membrane.

It is a further object of the invention to provide an improved method of returning an incised corneal flap to its original position.

It is a further object of this invention to provide a method by which the corneal flap can be retracted to one side while the underlying bed is treated.

It is further object of the invention to reposition the flap over the underlying treated area.

These and other objects of the invention will become clear to one skilled in the art upon reading the detailed description and appended claims in view of the provided figures.

SUMMARY OF THE INVENTION

The invention comprises a micro-keratome which places a lamellar corneal incision creating a hinged corneal flap. The device of the invention is capable of maintaining near physiologic hydration of the hinged flap and holds the corneal flap to one side to allow corneal treatment while the device is in position. The device then repositions and reattaches the corneal cap. The cutting treatment and flap re-attachment are all performed without removing the micro-keratome from the globe. The bulk of the cutting portion of the micro-keratome, or the entire cutting portion of the micro-keratome, remains attached to the vacuum ring during the entire procedure.

The device of the invention is also capable of inducing various levels of vacuum in order to fixate the globe of the eye during various steps of the procedure. For example, during cutting, higher levels of vacuum are used than the lower levels used during the step in which the corneal cap is peeled back for further treatment.

An embodiment of the invention holds the corneal flap in position after cutting to reduce stress and facilitate flap replacement and reattachment. The invention utilizes various materials for the cutting edge, including steel edges and gemstone blades made from diamond, sapphire, ruby and the like. The cutting blade movement can be controlled with ultrasound, hydraulics, flexible drive shafts, cam shafts, worm gears or electric motors or other means. Real time feed back can be utilized to independently control the blade movement in two dimensions—the speed of the blade within the blade carrier and the speed of the keratome across the corneal surface. Laser pachymetry may also be utilized to monitor the corneal changes during the procedure. Real time topographic and/or refractive feedback can also be used.

Embodiments of the device may also incorporate laser beam shaping systems, components to remove the ablation by-products, and/or components to add corneal tissue, synthetic materials, natural materials, fluid, medications, and the like, to the cornea prior to reattaching the cap.

DETAILED DESCRIPTION OF THE INVENTION AND THE PREFERRED EMBODIMENTS

Figure 1A:
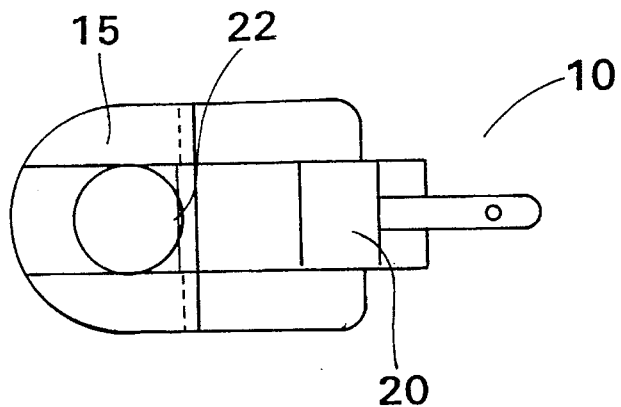
FIG. 1A is a top view of a micro-keratome to be utilized in the process according to the invention.
Figure 1B:
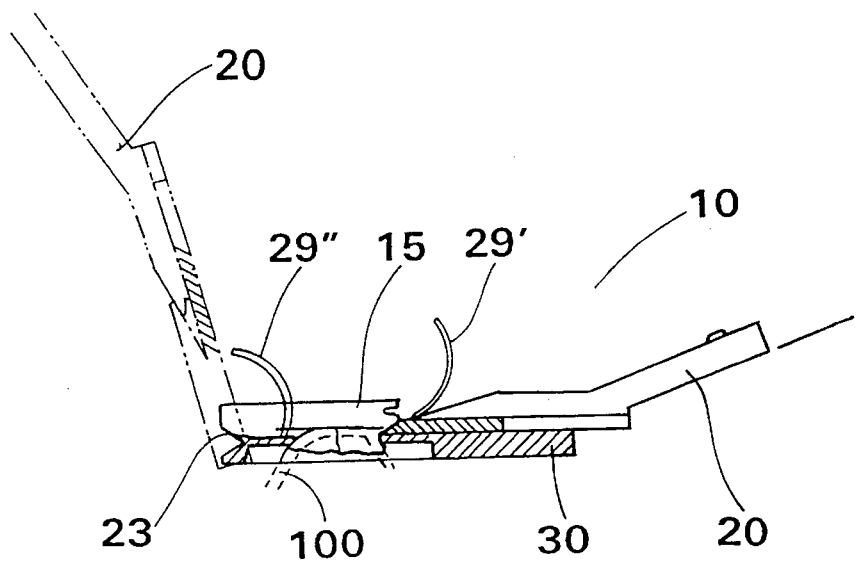
FIG. 1B is a side view of a micro-keratome to be utilized in the process according to the invention.
Figure 1C:
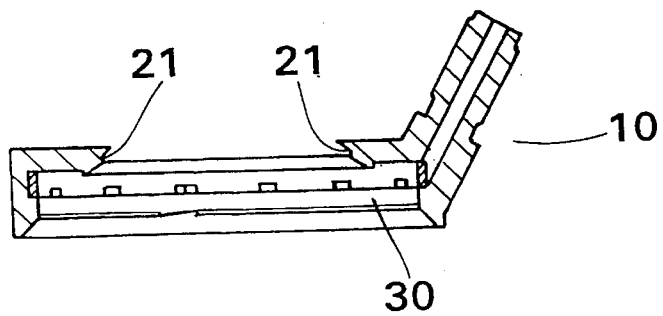
FIG. 1C is a side view of the vacuum ring of the micro-keratome of FIGS. 1A and 1B.

Referring to FIGS. 1A, 1B and 1C, the microkeratome 10 comprises an applanation shoe 15 and a knife carrier slide 20 in dovetail arrangement mounted to a vacuum ring 30 for mounting micro-keratome 10 to the globe of the eye 100 of a patient. After vacuum mounting micro-keratome 10 and knife carrier slide 20 traverse through dovetailed channel 21 in applanation shoe 15. Knife blade 22 incises cornea from globe, removing a membranous layer of desired thickness. Knife carrier slide 20 can be moved in response to mechanical, manual or other stimulus (not shown). The incised membrane layer is maintained by curved retracting guard 29. Curved retracting guard 29 moves with knife carrier slide 20 during cutting. Curved retracting guard 29 starts at position 29' in FIG. 1B and ends at position 29" after cutting.

After cutting, blade 22 is retracted and the assembly comprising knife carrier slide 20 and applanation shoe 15 is pivoted out (as shown in phantom, in FIG. 1B). The assembly pivots about axle 23 on vacuum rings to provide a clear optical path for laser ablation without removing vacuum ring 30 from the patient's eye. Ablation laser (not shown) comprises any commercial surgical laser, for example excimer 193 nm laser, Yag frequency quintupled laser, 193nm solid state laser, or any laser of a wavelength absorbed by corneal tissue. Examples of such lasers are extant lasers available from Summit or Visx. In this, and other embodiments, carrier slide 20, as well as other components, may be fabricated from an optically clear material that has high transmission of laser of a wavelength absorbable by the cornea.

Figure 2A:
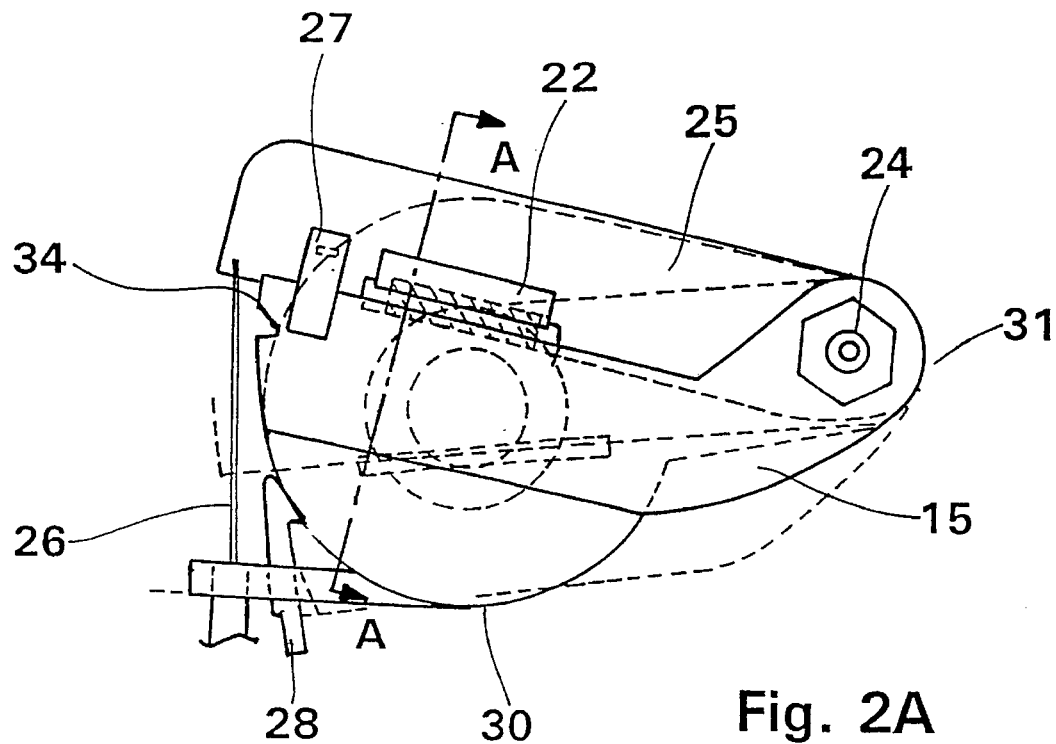
FIG. 2A is a second embodiment of the micro-keratome to be utilized in the process according to the invention, before the incision step.

Referring to FIG. 2A, in this embodiment, the knife carrier 25, holding blade 22, and the applanation assembly 15 are all mounted in an assembly 31 containing a single pivot 24. The assembly 31 is carried on the structure of vacuum ring 30. Rotary cutting motion as exhibited in this embodiment is inherently more accurate and easier to implement than the linear motion shown in FIG. 1. Rotation of knife carrier 25 about pivot 24 incises the cornea with a rotary motion.

Figure 2D:
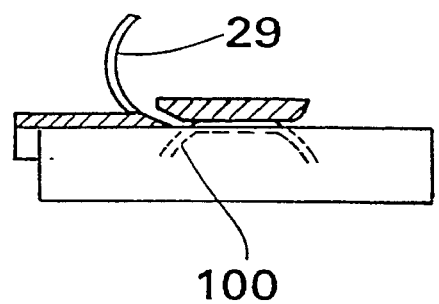
FIG. 2D is a side view of FIG. 2A taken along lines A—A.
Figure 2C:
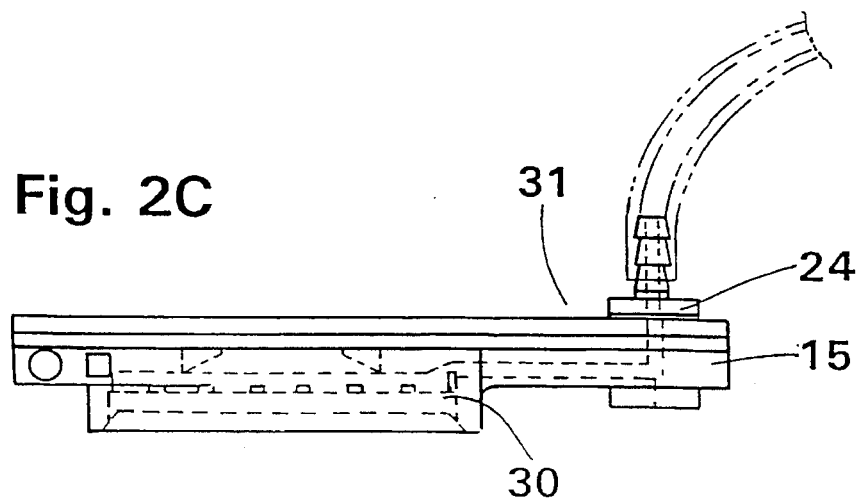
FIG. 2C is a side view of the vacuum ring of the micro-keratome of FIGS. 2A and 2B.
Figure 2B:
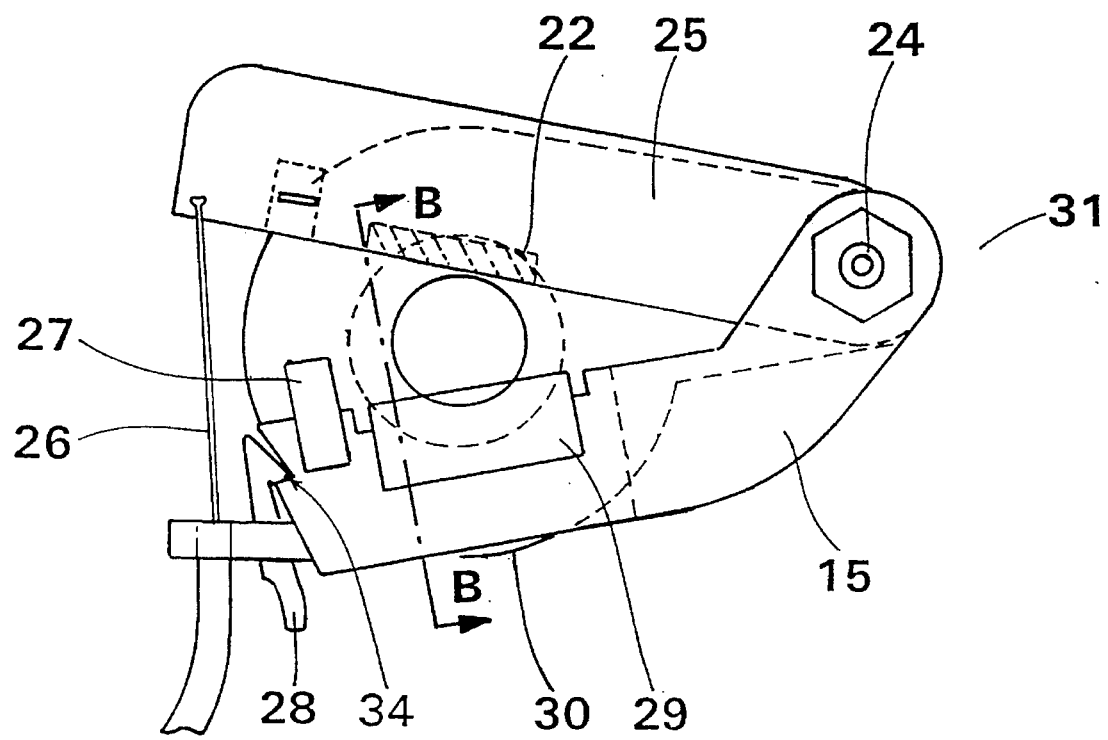
FIG. 2B is the micro-keratome of FIG. 2A after the incision step.

In FIGS. 2A–B, knife carrier 25 and applanation assembly 15 are actuated by a flexible linear cable 26 connected to a remote linear actuator (not shown). Spring loaded latch 27 holds the knife carrier 25 and applanation assembly 15 together during the cutting operation as shown in FIG. 2A. The latched knife carrier 25 and applanation assembly 15, as a unit, rotates about pivot 24 to cut cornea. FIGS. 3A–D show the motion of the unit across the eye during cutting. Cutting is limited by means of a stop 32 so that the membrane is not completely detached from the cornea.

At the end of cutting operation, when flexible linear cable 26 is fully retracted, latch 27 is opened (unlatched) by means of a dog (not shown) mounted on the structure of the vacuum ring 30. At the same time cutting is completed, second spring loaded latch 28 snaps into a notch 34 on applanation assembly 15, holding this assembly in the position shown in FIGS. 2B and 3D.

Figure 3A:
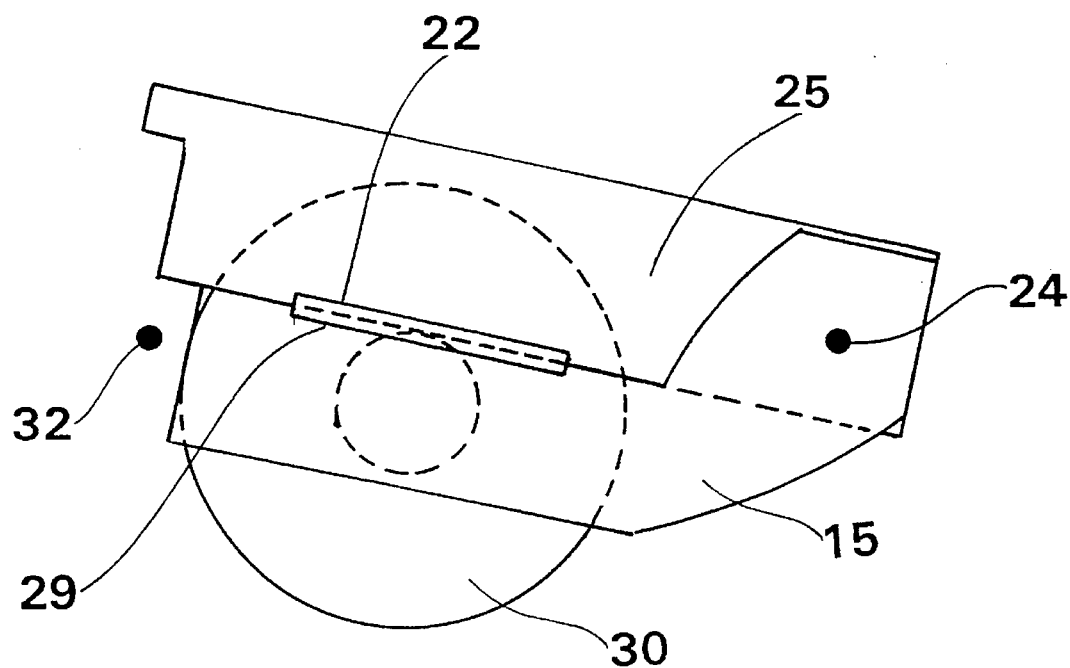
FIGS. 3A–D illustrate the cutting operation sequence of the micro-keratome of FIGS. 2A–C.
Figure 3B:
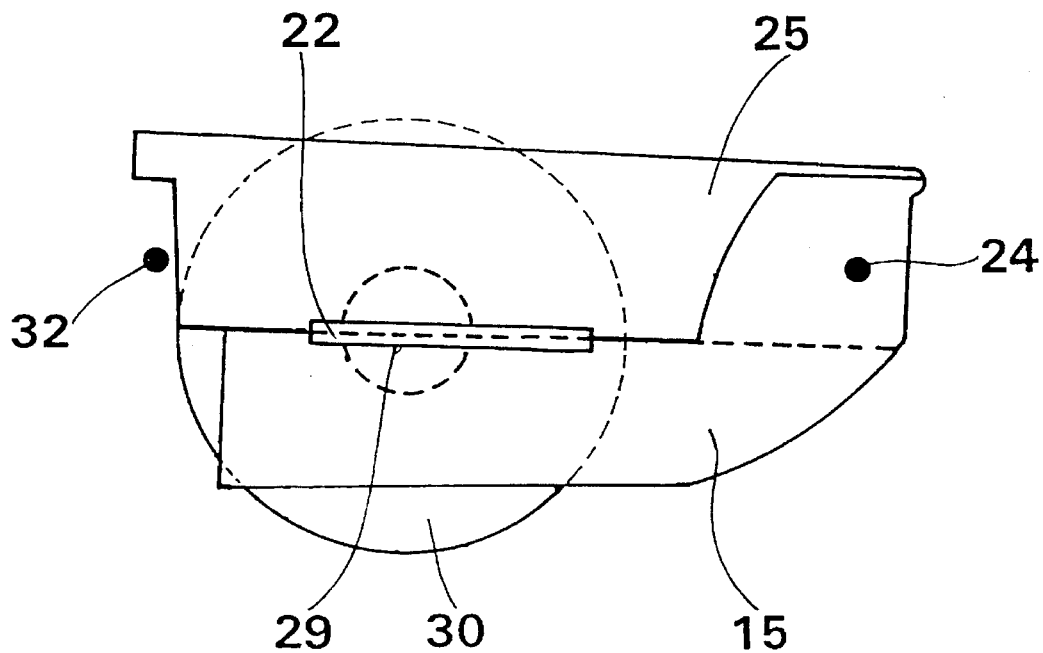
Figure 3C:
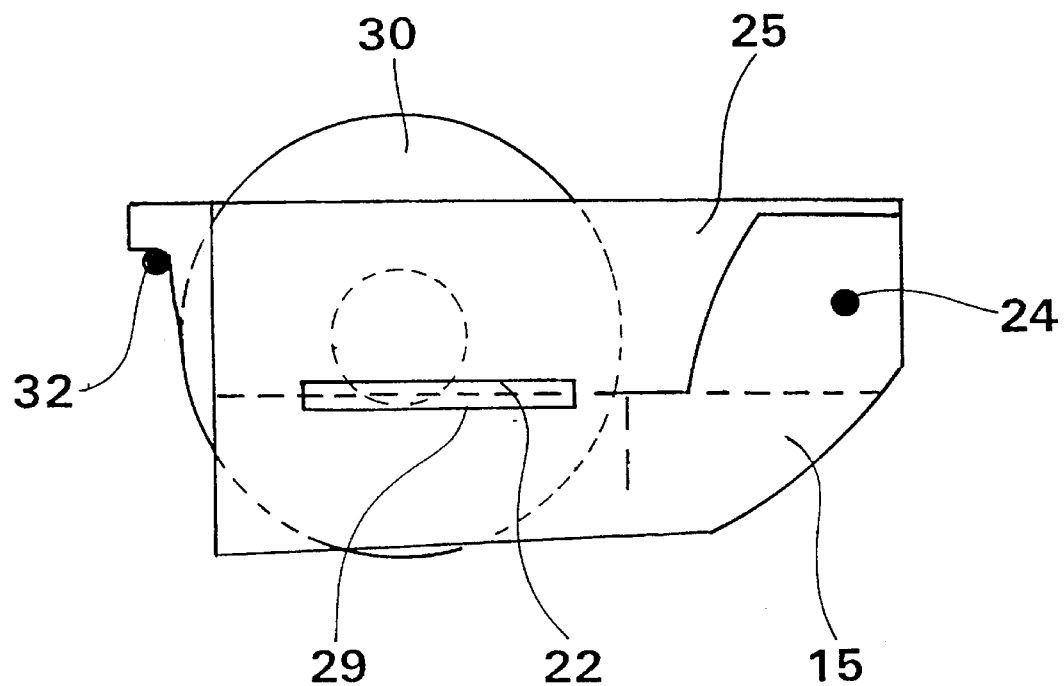
Figure 3D:
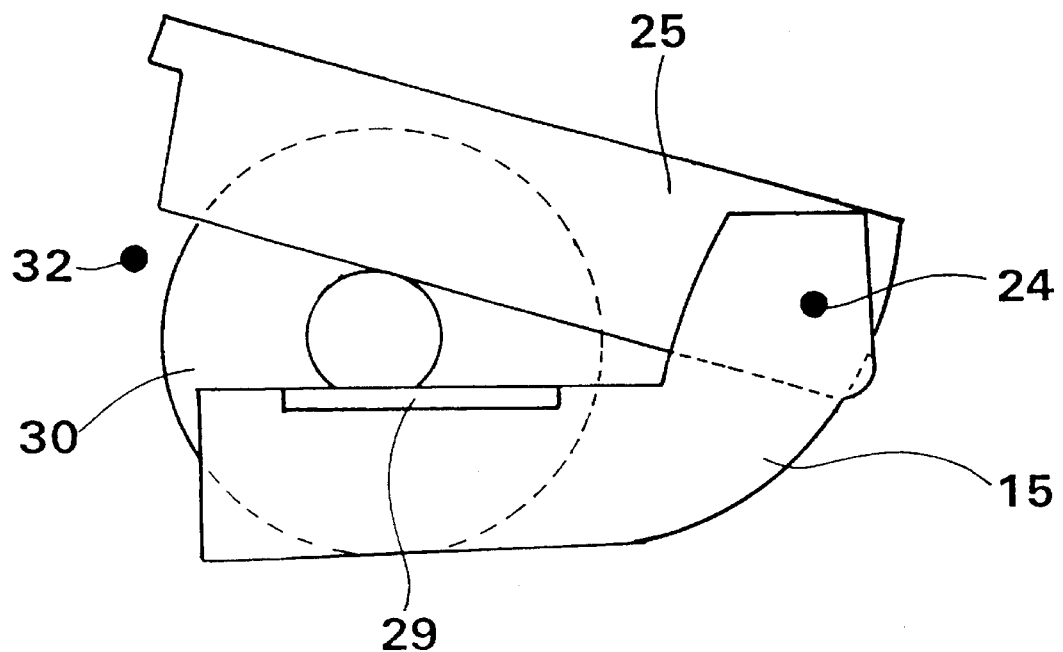

Flexible linear cable 26 is then fully extended, pivoting knife carrier 25 back to the initial position shown in FIGS. 2B and 3D. In this position knife carrier 25 and applanation assembly 15 allow laser (not shown) to irradiate the exposed cornea.

Figure 2E:
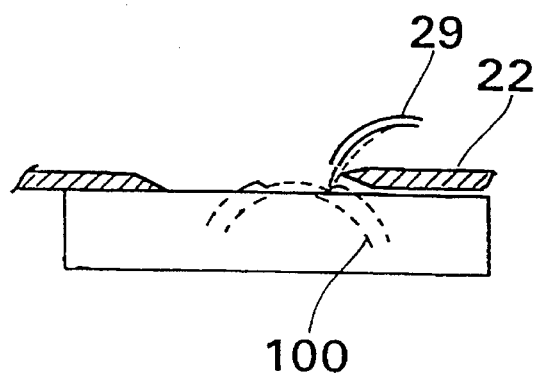
FIG. 2E is a side view of FIG. 2B taken along lines B—B.

Curved retracting guard 29 is also rotatively mounted on applanation assembly 10 to collect, protect and position the membrane removed from the cornea. As shown in FIG. 2D, retracting guard 29 is positioned to collect the membrane during the cutting operation. At the end of the cutting operation, as shown in FIG. 2E, curved retracting guard 29 is rotated about a pivot (not shown) to position the membrane so as to provide a clear path from the laser to the cornea. The same means used to actuate latch 27 will also be used to actuate curved retracting guard 29. As shown in FIG. 2C, pivot 24 has a hollow center which communicates with vacuum ring 30.

The vacuum ring portion of the keratome of the invention is capable of exerting variable vacuum pressure on the globe. Prior art vacuum apparatus only exerted a single vacuum pressure when mounted to the globe. Variable vacuum pressure allows the vacuum ring used in the micro-keratome of the invention to remain mounted to the globe during the entire surgical procedure. This allows a lower suction level and associated fixation during laser ablation and a high suction level during micro-keratome cutting and during flap repositioning. Micro-keratome and vacuum ring removal are not required during ablation. This maintains better flap hydration and allows better flap repositioning.

By allowing the cutting portion of the micro-keratome to be removed from the laser path while remaining mounted to the globe of the eye, laser ablation can be performed on the exposed corneal areas without mechanically disassembling the micro-keratome and/or the vacuum device. Other embodiments facilitate production of an unobstructed optical path for the laser beam. For example, portions of the cutting apparatus or the cutting blade could be prepared from an optically transparent material. Optically transparent means a material capable of transmitting laser light of a wavelength absorbable by the cornea and include an absence of material in the laser path.

The micro-keratome of the invention is useful in a variety of procedures. Such procedures include further corneal incisions, removal of corneal tissue, addition of tissue (either synthetic or natural) to the cornea, laser ablation, and other laser treatments and introduction of hydration or liquid medication. The current invention can be utilized in treating a variety of medical conditions including myopia, hyperopia, astigmatism, presbyopia and a variety of corneal surface abnormalities, including corneal scars, corneal dystrophies and keratoconus.

The micro-keratome of the invention may incorporate a variety of feedback systems to monitor the progress of various stages of the surgical procedure. Real time feedback can assess and maintain proper cutting speed of the blade within the carrier, as well as the velocity of travel of the micro-keratome in making the corneal incision. Real time topographic and refractive feedback can be utilized to monitor laser and treatment progress. A laser pachymeter can be incorporated to measure change in corneal (or other material) thickness. Laser pachymetric feedback provides a calibration system to constantly monitor laser progress during corneal manipulation. Laser pachymetric feedback systems are possible with the current invention wherein an unobstructed path for laser beams has been provided.

Although particular embodiments of the present invention have been illustrated and described, it would be obvious to those skilled in the art that various other changes and modifications can be made without departing from the spirit and scope of the invention. Therefore, it is intended to cover in the appended claims all such changes and modifications that are within the scope of this invention.

We claim:

1. A micro-keratome comprising a vacuum ring, an applanation shoe and a cutting blade, wherein said cutting blade and applanation shoe are mounted on said vacuum ring, said cutting blade being pivotally mounted to said applanation shoe to allow movement of said cutting blade while said vacuum ring is mounted to a patient's eye, to provide an unobstructed path to a corneal layer exposed by said cutting blade.

2. The micro-keratome of claim 1 wherein said cutting blade comprises a surgical steel cutting edge.

3. The micro-keratome of claim 1 wherein said cutting blade comprises at least one cutting surface prepared from gemstones, said gemstones being chosen from the group consisting of diamond, sapphire, or ruby.

4. The micro-keratome of claim 1 wherein the unobstructed path is a clear optical path for laser ablation of said exposed corneal layer.

5. The micro-keratome of claim 1 further comprising real time feedback analyzer means to monitor a cutting motion of said blade and said micro-keratome.

6. A micro-keratome that allows passage of a surgical laser beam therethrough, said micro-keratome comprises a vacuum ring, an applanation shoe and a cutting blade pivotally mounted to said applanation shoe whereby movement of said cutting blade does not require removal of said vacuum ring from a patient's eye to provide an unobstructed path to a corneal layer exposed by said cutting blade.

7. The micro-keratome of claim 1, further comprising real time feedback analyzer means to monitor a motion of said cutting blade.

8. The micro-keratome of claim 1, wherein said cutting blade has at least a portion thereof prepared from an optically transparent material.

9. The micro-keratome of claim 1, wherein said cutting blade is mounted in a carrier having at least a portion thereof prepared from an optically transparent material.

10. The micro-keratome of claim 1, wherein said vacuum ring is capable of producing different vacua during movement and nonmovement period of said blade.

11. A micro-keratome device comprising:

a vacuum ring that secures the device to an eye;

an applanation shoe attached to a top portion of the vacuum ring and held in a fixed position above the eye;

a cutting blade carrier mounted at one end of the applanation shoe;

a cutting blade held within the cutting blade carrier for surgically cutting a selected portion of the eye; and a guard mounted at one end of the applanation shoe for movement with but independent of the cutting blade carrier, and for collecting, protecting, and positioning the selectively cut eye portion tissue;

whereby the cutting blade is movable independently of and retractable into the cutting blade carrier, and the cutting blade carrier and the guard move to provide an unobstructed pathway to the surgically exposed eye without removal of the vacuum ring from the eye.

12. The device of claim 11, wherein said cutting blade comprises at least one cutting surface prepared from gemstones, said gemstones being chosen from the group consisting of diamond, sapphire, or ruby.

13. The device of claim 11, wherein the unobstructedu path is a clear optical path for laser ablation of said exposed eye.

14. The device of claim 11, further comprising real time feedback analyzer means to monitor a cutting motion of said cutting blade with respect to said cutting blade carrier.

15. The device of claim 11, further comprising real time feedback analyzer means to monitor a motion of said cutting blade carrier.

16. The device of claim 11, further comprising laser pachymeter apparatus to monitor the extent of laser ablation of said exposed eye.

17. The device of claim 11, wherein said cutting blade has at least a portion thereof prepared from an optically transparent material.

18. The device of claim 11, wherein said cutting blade carrier has at least a portion thereof prepared from an optically transparent material.

19. The device of claim 11, wherein said vacuum ring is capable of producing different vacua during movement and nonmovement periods of said blade.

20. The device of claim 11 wherein said cutting blade carrier is permanently mounted to said vacuum ring.

21. The device of claim 11 wherein said cutting blade carrier is pivotally attached to said applanation shoe, allowing said cutting blade carrier to be pivoted out of said unobstructed pathway during said surgical procedure, after said incision is made.

22. The device of claim 21 wherein said cutting blade carrier pivots away from said cornea through an angle to a plane projected by said applanation shoe as mounted on said vacuum ring.

23. The device of claim 22 wherein said cutting blade carrier can pivot independent of said guard.

24. The device of claim 21 wherein said applanation shoe is pivotally connected to said vacuum ring allowing pivoting motion of said applanation shoe in a plane substantially parallel to a plane projected by said applanation shoe as mounted on said vacuum ring.

25. The device of claim 24 further comprising a stop to limit the movement of said cutting blade carrier.

26. The device of claim 24 wherein said cutting blade carrier moves about said pivotal attachment in a plane substantially parallel to a plane projected by said applanation shoe as mounted on said vacuum ring.

27. The device of claim 26 further comprising a stop to limit the movement of said cutting blade carrier.

28. The device of claim 27 wherein said pivotal attachment of said applanation shoe and said pivotal connection of said cutting blade carrier pivot about the same axis, and said cutting blade carrier and said applanation shoe further comprise means for interlocking said cutting blade carrier and said applanation shoe, one with the other, to allow simultaneous movement of said interlocked cutting blade carrier and applanation shoe in a plane substantially parallel to a plane projected by said vacuum ring as said cutting blade makes said incision, said movement traversing from a first position prior to making said incision wherein said cutting blade carrier and said applanation shoe are interlocked, to a second position, after making said incision, at which point said stop limits movement of said applanation shoe and said cutting blade carrier and said applanation shoe remain interlocked.

29. The device of claim 28 further comprising means for releasing said interlocking means after said incision is made, when said cutting blade carrier and said applanation shoe are at said second position, said releasing means returning said cutting blade carrier to said first position while said applanation shoe remains in said second position.

30. The device of claim 27 wherein said pivotal attachment of said applanation shoe and said pivotal connection of said cutting blade carrier pivot about the same axis, and said cutting blade carrier and said applanation shoe further comprise means for interlocking said cutting blade carrier and said applanation shoe, one with the other, to allow simultaneous movement of said interlocked cutting blade carrier and applanation shoe in a plane substantially parallel to a plane projected by said vacuum ring as said cutting blade makes said incision, said movement traverses from a first position prior to making said incision wherein said cutting blade carrier and said applanation shoe are interlocked, to a second position, after making said incision, at which point said cutting blade carrier and said applanation shoe remain interlocked.

31. The device of claim 30 further comprising means for releasing said interlocking means after said incision is made, when said cutting blade carrier and said applanation shoe are at said second position, said releasing means returning said cutting blade carrier to said first position while said applanation shoe remains in said second position.

32. The device of claim 11 wherein said cutting blade carrier is slidably mounted to a sub-assembly comprising said vacuum ring and said applanation shoe.

33. The device of claim 32 wherein said slidable mounting comprises at least one channel on said sub-assembly which corresponds with the same number of runner(s) on said cutting blade carrier said runner(s) engaging said channel(s) to provide a controlled pathway to guide the slidable movement of said cutting blade carrier with respect to said sub-assembly.

34. The device of claim 33 wherein said channel(s) and said runner(s) engage in a dove-tail configuration.

35. The device of claim 33, wherein said cutting blade carrier is permanently mounted to said vacuum ring.

36. The device of claim 32 wherein said cutting blade carrier is releasably mounted to said sub-assembly.

37. The device of claim 36 wherein said slidable mounting comprises at least one channel on said sub-assembly which corresponds with the same number of runner(s) on said cutting blade carrier said runner(s) engaging said channel(s) to provide a controlled pathway to guide the slidable movement of said cutting blade carrier with respect to said sub-assembly.

38. The device of claim 37 wherein said channel(s) and said runner(s) engage in a dove-tail configuration.

39. A micro-keratome device comprising:

a vacuum ring, a cutting blade carrier containing a cutting blade, a guard, and an applanation shoe, wherein said cutting blade carrier, said cutting blade and said applanation shoe are mounted on said vacuum ring; said cutting blade is movable independently of said cutting blade carrier so that after making an incision in a cornea of a patient, said cutting blade can be retracted into said cutting blade carrier; said guard maintains incised portions of said cornea during an ophthalmic surgical procedure to be performed on said patient and returns said incised portion to said cornea after said surgical procedure; and said micro-keratome provides an unobstructed pathway to layers of said cornea exposed by displacement of said incised portions without removing said cutting blade carrier from said micro-keratome prior to or during said surgical procedure;

wherein said applanation shoe is pivotally connected to said vacuum ring allowing pivoting motion of said applanation shoe in a plane substantially parallel to a plane projected by said applanation shoe as mounted on said vacuum ring;

wherein said cutting blade carrier is pivotally attached to said applanation shoe, allowing said cutting blade carrier to be pivoted out of said unobstructed pathway during said surgical procedure, after said incision is made;

wherein said micro-keratome further comprises a stop to limit the movement of said cutting blade carrier;

wherein said pivotal attachment of said applanation shoe and said pivotal connection of said cutting blade carrier pivot about the same axis, and said cutting blade carrier and said applanation shoe further comprise means for interlocking said cutting blade carrier and said applanation shoe, one with the other, to allow simultaneous movement of said interlocked cutting blade carrier and applanation shoe in a plane substantially parallel to a plane projected by said vacuum ring as said cutting blade makes said incision, said movement traversing from a first position prior to making said incision wherein said cutting blade carrier and said applanation shoe are interlocked, to a second position, after making said incision, at which point said stop limits movement of said applanation shoe and said cutting blade carrier and said applanation shoe remain interlocked; and said micro-keratome further comprises means for releasing said interlocking means after said incision is made, when said cutting blade carrier and said applanation shoe are at said second position, said releasing means returning said cutting blade carrier to said first position while said applanation shoe remains in said second position.

40. The device of claim 39, wherein said cutting blade has at least a portion thereof prepared from an optically transparent material.

41. The device of claim 40, wherein said cutting blade carrier has at least a portion thereof prepared from an optically transparent material.

42. A micro-keratome device comprising:

a vacuum ring, a cutting blade carrier containing a cutting blade, a guard, and an applanation shoe, wherein said cutting blade carrier, said cutting blade and said applanation shoe are mounted on said vacuum ring; said cutting blade is movable independently of said cutting blade carrier so that after incising a cornea of a patient, said cutting blade can be retracted into said cutting blade carrier; said guard maintains incised portions of said cornea during an ophthalmic surgical procedure to be performed on said patient and returns said incised portion to said cornea after said surgical procedure; and said micro-keratome provides an unobstructed pathway to layers of said cornea exposed by displacement of said incised portions;

wherein said cutting blade carrier is pivotally attached to said applanation shoe, allowing said cutting blade carrier to be pivoted out of said unobstructed pathway during said surgical procedure, after said incision is made;

wherein said pivotal attachment allows pivoting motion of said cutting blade carrier away from said cornea through an angle to a plane projected by said applanation shoe as mounted on said vacuum ring; and wherein said cutting blade carrier is slidably mounted to a sub-assembly comprising said vacuum ring and said applanation shoe, said slidable mounting comprising at least one channel on said subassembly corresponding with the same number of runner(s) on said cutting blade carrier, said runner(s) engaging said channel(s) to provide a controlled pathway to guide the slidable movement of said cutting blade carrier with respect to said sub-assembly.

43. The device of claim 42, wherein said cutting blade carrier has at least a portion thereof prepared from an optically transparent material.

44. The device of claim 43, wherein said cutting blade has at least a portion thereof prepared from an optically transparent material.

* * * * *